United States Patent
Kunzler

(10) Patent No.: US 7,537,612 B2
(45) Date of Patent: May 26, 2009

(54) LUMBAR COMPOSITE NUCLEUS

(75) Inventor: Alex Kunzler, Issaquah, WA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 487 days.

(21) Appl. No.: 10/938,043

(22) Filed: Sep. 10, 2004

(65) Prior Publication Data

US 2005/0038515 A1    Feb. 17, 2005

Related U.S. Application Data

(63) Continuation-in-part of application No. 10/600,052, filed on Jun. 20, 2003.

(51) Int. Cl.
  *A61F 2/44* (2006.01)
(52) U.S. Cl. .................. 623/17.13; 623/17.15
(58) Field of Classification Search .... 623/17.11–17.16
  See application file for complete search history.

(56) References Cited

U.S. PATENT DOCUMENTS

| | | | |
|---|---|---|---|
| 4,309,777 A | 1/1982 | Patil | |
| 4,759,769 A | 7/1988 | Hedman et al. | |
| 4,932,969 A | 6/1990 | Frey et al. | |
| 5,002,576 A | 3/1991 | Fuhrmann et al. | |
| 5,123,926 A | 6/1992 | Pisharodi | |
| 5,320,644 A | 6/1994 | Baumgartner | |
| 5,401,269 A * | 3/1995 | Buttner-Janz et al. | 623/17.15 |
| 5,458,642 A | 10/1995 | Beer et al. | |
| 5,674,294 A | 10/1997 | Bainville et al. | |
| 5,702,450 A | 12/1997 | Bisserie | |
| 5,782,832 A | 7/1998 | Larsen et al. | |
| 5,827,328 A | 10/1998 | Buttermann | |
| 5,893,889 A | 4/1999 | Harrington | |
| 5,928,284 A | 7/1999 | Mehdizadeh | |
| 6,231,609 B1 | 5/2001 | Mehdizadeh | |
| 6,290,726 B1 | 9/2001 | Pope et al. | |
| 6,395,034 B1 | 5/2002 | Suddaby | |
| 6,402,785 B1 | 6/2002 | Zdeblick et al. | |
| 6,454,806 B1 | 9/2002 | Cohen et al. | |
| 6,468,310 B1 | 10/2002 | Ralph et al. | |
| 6,527,804 B1 * | 3/2003 | Gauchet et al. | 623/17.12 |
| 6,533,817 B1 | 3/2003 | Norton et al. | |
| 6,579,321 B1 | 6/2003 | Gordon et al. | |
| 6,592,624 B1 | 7/2003 | Fraser et al. | |
| 6,602,291 B1 | 8/2003 | Ray et al. | |
| 6,607,558 B2 | 8/2003 | Kuras | |
| 6,610,092 B2 | 8/2003 | Ralph et al. | |
| 6,610,093 B1 | 8/2003 | Pisharodi | |
| 6,626,943 B2 | 9/2003 | Eberlein et al. | |
| 6,656,224 B2 | 12/2003 | Middleton | |
| 6,666,890 B2 | 12/2003 | Michelson | |
| 6,673,113 B2 * | 1/2004 | Ralph et al. | 623/17.13 |
| 6,682,562 B2 * | 1/2004 | Viart et al. | 623/17.14 |
| 6,712,853 B2 | 3/2004 | Kuslich | |
| 6,719,796 B2 | 4/2004 | Cohen et al. | |
| 6,723,127 B2 * | 4/2004 | Ralph et al. | 623/17.13 |
| 6,981,989 B1 * | 1/2006 | Fleischmann et al. | 623/17.11 |

(Continued)

*Primary Examiner*—Pedro Philogene
(74) *Attorney, Agent, or Firm*—Haynes and Boone, LLP

(57) ABSTRACT

A prosthetic device for insertion into an intervertebral disc space is provided. The device includes a first endplate component for engaging a first vertebral body, a second endplate component for engaging a second vertebral body, and an articulating central body component extending between the first and second endplate components. The articulating central body component having a mechanical compression component.

23 Claims, 2 Drawing Sheets

U.S. PATENT DOCUMENTS

| | | | |
|---|---|---|---|
| 7,025,787 B2 * | 4/2006 | Bryan et al. | 623/17.16 |
| 7,066,958 B2 * | 6/2006 | Ferree | 623/17.12 |
| 7,250,060 B2 * | 7/2007 | Trieu | 623/17.15 |
| 2003/0074076 A1 | 4/2003 | Ferree et al. | |
| 2003/0187506 A1 | 10/2003 | Ross et al. | |
| 2004/0002761 A1 | 1/2004 | Rogers et al. | |
| 2004/0002762 A1 | 1/2004 | Hawkins | |
| 2004/0024460 A1 | 2/2004 | Ferree | |
| 2004/0024461 A1 | 2/2004 | Ferree | |
| 2004/0030391 A1 | 2/2004 | Ferree | |
| 2004/0044410 A1 | 3/2004 | Ferree et al. | |
| 2005/0251260 A1 * | 11/2005 | Gerber et al. | 623/17.13 |

* cited by examiner

LUMBAR COMPOSITE NUCLEUS

CROSS-REFERENCE

This is a continuation-in-part to U.S. Ser. No. 10/600,052 titled Wear-Resistant Endoprosthetic Devices, filed on Jun. 20, 2003, assigned to the same entity as the present patent, and herein incorporated by reference as if reproduced in its entirety.

BACKGROUND

The present disclosure relates generally to prosthetic devices, and in particular, to articulated endoprosthetic devices, such as those suitable for implantation into the intervertebral space between adjacent vertebrae of the spinal column.

In the treatment of diseases, injuries or malformations affecting spinal motion segments, and especially those affecting disc tissue, it has long been known to remove some or all of a degenerated, ruptured or otherwise failing disc. Currently, the standard treatment remains disectomy followed by vertebral fusion. While this approach may alleviate a patient's present symptoms, accelerated degeneration of adjacent discs is a frequent consequence of the increased motion and forces induced by fusion.

Therefore, what is needed is an artificial intervertebral prosthetic device, which includes wear-resistant articulating surfaces that provide bio-mechanical action mimicking the movement of the natural intervertebral disc, as well as a shock-absorbing body, in order to reduce deterioration of the adjacent discs.

SUMMARY

In one embodiment, a prosthetic device for insertion into an intervertebral space is provided. The device includes a first endplate component for engaging a first vertebral body, a second endplate component for engaging a second vertebral body, and an articulating central body component extending between the first and second endplate components. The articulating central body component includes a mechanical compression component. In some embodiments, the mechanical compression component is a wave spring washer.

In some embodiments, the prosthetic device includes an alignment key and an alignment groove member extending from an inner surface of one of the end caps to mate with the corresponding alignment key and groove member extending from an inner surface of the other end cap.

In some embodiments, the prosthetic device includes retaining posts disposed on the inner surfaces of the endplate components that extend through central openings of the articulating central body component.

In another embodiment, a system for replacing an intervertebral disc is provided. The system includes a first endplate component for engaging a first vertebral body, a second endplate component for engaging a second vertebral body, and an articulating central body component interposed between the first and second endplate components. The articulating central body component includes a mechanical compression component. The articulating central body component provides motion between the first endplate component and the second endplate component.

In another embodiment, a surgical method is provided. The surgical method includes providing a first endplate component for engaging a first vertebral body, providing a second endplate component for engaging a second vertebral body, providing an articulating central body having a mechanical compression component, and inserting the articulating central body component between the first endplate component and the second endplate component. The articulating central body component includes a first end cap component that articulates with the first endplate component and a second end cap component that articulates with the second endplate component.

BRIEF DESCRIPTION OF THE DRAWINGS

FIG. 3b is a cross sectional side view of an assembled intervertebral disc prosthesis of FIG. 3a.

DESCRIPTION

Figure 1:
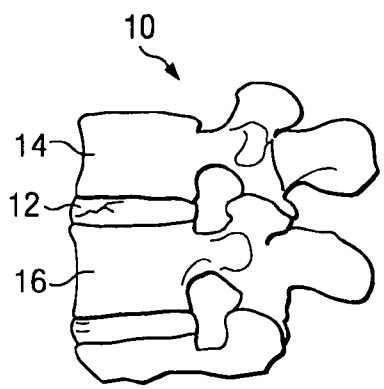
FIG. 1 is a lateral view of a portion of a vertebral column having a damaged disc.

The present invention relates generally to prosthetic devices, and more particularly, to a functional endoprosthetic device. For the purposes of promoting an understanding of the principles of the disclosure, reference will now be made to the embodiments, or examples, illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which this disclosure relates. As such, individual features of separately described embodiments can be combined to form additional embodiments.

Referring first to FIG. 1, the reference numeral 10 refers to a vertebral column with a damaged intervertebral disc 12 extending between two intact vertebrae 14 and 16. In a typical surgical discectomy, the damaged disc 12 is removed creating a void between the two intact vertebrae 14 and 16. This procedure may be performed using an anterior, anterolateral, lateral, or other approach known to one skilled in the art.

Figure 2:
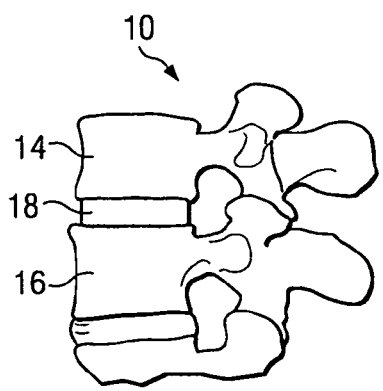
FIG. 2 is a lateral view of a portion of a vertebral column with an intervertebral disc prosthesis replacing the damaged disc of FIG. 1.

Referring now to FIG. 2, an endoprosthesis 18 may be provided to fill the void between the adjacent vertebrae 14 and 16.

Figure 3A:
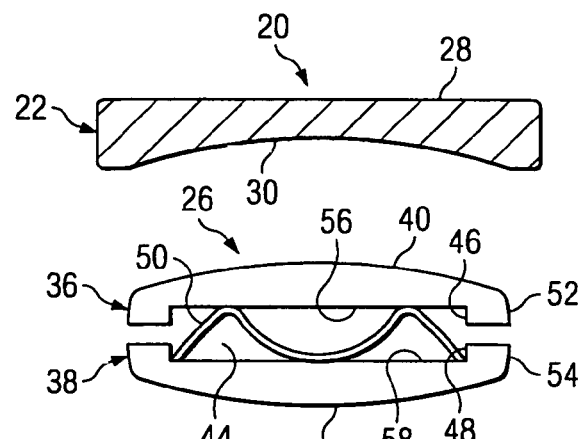
FIG. 3a is a cross sectional side view of an exploded intervertebral disc prosthesis according to one embodiment of the present disclosure.
Figure 3B:
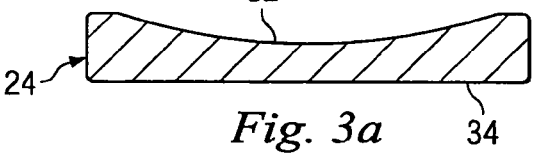
Figure 3B:
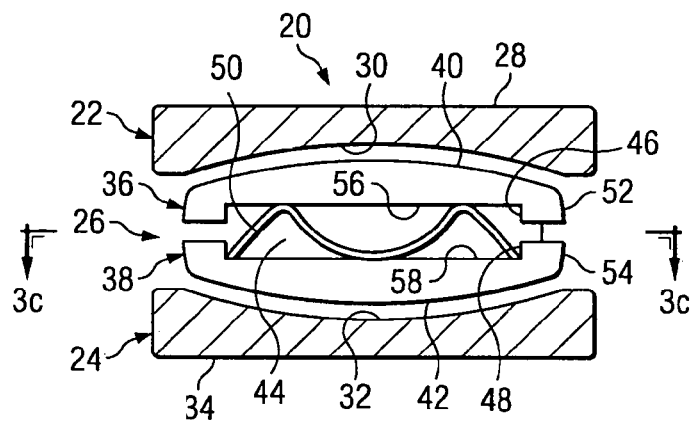
Figure 3C:
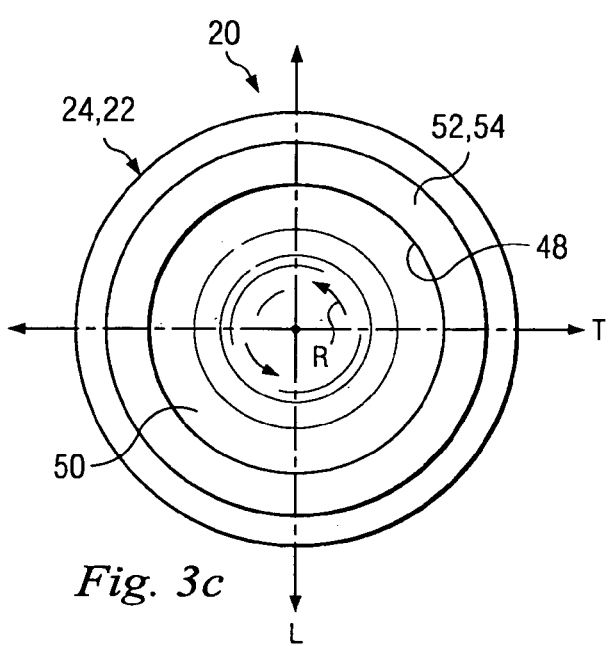
FIG. 3c is a cross sectional top view of the intervertebral disc prosthesis of FIG. 3b.

Referring now to FIGS. 3a, 3b, & 3c, shown therein is one embodiment of an intervertebral disc prosthesis 20 that may be used as the endoprosthesis 18 of FIG. 2. The intervertebral disc prosthesis 20, according to an embodiment of the present disclosure, includes endplate components 22, 24 and an articulating central body 26. The endplate components 22, 24 may include exterior surfaces 28, 34 and interior surfaces 30, 32. The endplate components 22, 24 are formed so as to contact the existing vertebrae body adjacent to the disc space, in a way that the endplate components 22, 24 are substantially immobilized with respect to the vertebrae. The vertebrae and the attached endplate components 22, 24 move together with respect to the articulating central body 26 as the interior surfaces 30, 32 articulate with respect to the articulating central body 26. The intervertebral disc prosthesis 20 provides relative pivotal and rotational movement between the adjacent vertebral bodies to maintain or restore motion substantially similar to the normal bio-mechanical motion provided by a natural intervertebral disc.

Although the endplate components 22, 24 of the intervertebral disc prosthesis 20 may be formed from a variety of materials, in one embodiment of the disclosure, the endplate components 22, 24 are formed of a cobalt-chrome metallic alloy. However, in alternative embodiments of the disclosure, the endplate components 22, 24 may be formed of other materials such as titanium or stainless steel, ceramic, or a polymeric material such as polyethylene, or any other biocompatible material that would be apparent to one of ordinary skill in the art. Furthermore, the interior surfaces 30, 32 of the endplate components 22, 24 may be treated to make them smooth, increase their lubricity, or both. For example, the interior surfaces 30, 32 may be polished, coated, or comprise inserts of material different from the remainder of the endplate components 22, 24, in order to provide a smooth, wear-resistant surface and decrease the likelihood of generating wear debris during articulation.

The endplate components 22, 24 each include an exterior surface 28, 34, respectively, that may be positioned in direct contact with vertebral bone and are preferably coated with a bone-growth promoting substance, such as, for example, a hydroxyapatite coating formed of calcium phosphate. Additionally, the exterior surfaces 28, 34 of the endplate components 22, 24, respectively, may be roughened prior to being coated with the bone-growth promoting substance to further enhance bone on-growth. Such surface roughening may be accomplished by way of, for example, acid etching, knurling, application of a bead coating, or other methods of roughening that would be apparent to one of ordinary skill in the art.

The articulating central body 26 may include end cap components 36, 38 having articulating surfaces 40, 42 and interior surfaces 56, 58, respectively, as shown in FIGS. 3a & 3b. The end cap components 36, 38 may further include outer radial surfaces 52, 54 and inner radial surfaces 46, 48, respectively. In this embodiment, the end cap components 36, 38 cooperate with each other and form a recess compartment 44. The recess compartment 44 may be defined by the interior surfaces 56, 58 and the inner radial surfaces 46, 48 of the end cap components 36, 38. The articulating central body 26 may further include a mechanical compression component 50 which may be housed in the recess compartment 44, as shown in FIGS. 3a & 3b.

Although, the end cap components 36, 38 of the articulating central body 26 may be formed from a variety materials, in one embodiment of the disclosure, the end cap components 36, 38 are formed of a cobalt-chrome metallic alloy. However, in alternative embodiments of the disclosure, the end cap components 36, 38 may be formed of other materials such as titanium or stainless steel, ceramic, or a polymeric material such as polyethylene, or any other biocompatible material that would be apparent to one of ordinary skill in the art. Furthermore, the end cap components 36, 38 may be preferably shaped to provide smooth and wear-resistant articulating surfaces 40, 42 for contact with the corresponding endplate components 22, 24.

The articulating surfaces 40, 42 of the end cap components 36, 38 may be modified, treated, coated or lined to enhance the wear resistant and articulation properties of the articulating central body 26. These wear resistant and articulation properties may be provided by cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may be suitable. Polymer materials may also be used including any member of the PAEK family such as PEEK, carbon-reinforced PAEK, or PEKK; polysulfone; polyetherimide; polyimide; UHMWPE; and/or cross-linked UHMWPE. Polyolefin rubbers, polyurethanes, copolymers of silicone and polyurethane, and hydrogels may also provide wear resistance and articulation properties. Wear resistant characteristics may also or alternatively be provided to the articulating surfaces 40, 42 by modifications such as cross-linking and metal ion implantation.

The mechanical compression component 50 may be retained in the recess compartment 44 of the articulating central body 26 by securing the mechanical compression component 50 to one of the interior surfaces 56, 58 of the end cap components 36, 38, respectively. For example, the securing means may be provided by screws, clamps, or any other type of securing pins (not shown).

Although the embodiments of FIGS. 3a, 3b, & 3c show circular shaped endplate components 22, 24, and circular shaped mechanical compression components 50 other geometries may be square, oval, triangular, hexagonal, or any other shape. Furthermore, as shown in the cross sectional top view of FIG. 3c, the geometry of the end cap components 36, 38 of the articulating central body 26 may be round, oval, or any other shape which promotes constraint or articulation.

Referring to FIG. 3b, the intervertebral disc prosthesis 20 may be assembled by positioning the articulating central body 26 in between the endplate components 22, 24. The assembled prosthesis 20 may be implanted into the vertebral column 10 of FIG. 1 in the void created by the removed disc 12 such that the exterior surface 28 of the first endplate component 22 engages an endplate of the vertebral body 14 and the exterior surface 34 of the other endplate component 24 engages an endplate of the vertebral body 16. The articulating central body 26 may simply be contained within the endplate components 22, 24 by the natural compressive forces of the spinal column exerted on the endplate components 22, 24. In addition, the central body 26 may further be contained within the endplate components 22, 24 by the shape and design of the endplate components 22, 24.

Figure 4:
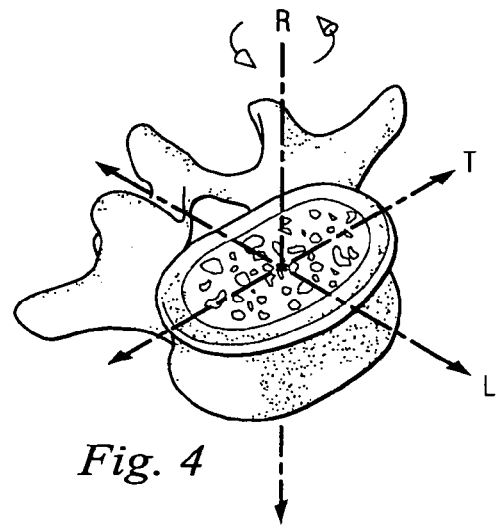
FIG. 4 is a perspective view of a vertebral body showing axes of movement.

Referring now to FIGS. 3c & 4, in operation, the intervertebral disc prosthesis 20 extends generally along a longitudinal axis L corresponding to the anterior-posterior aspect of the vertebral column 10 of FIG. 1 and along a transverse axis T corresponding to the lateral aspect of the vertebral column 10 of FIG. 1. The intervertebral disc prosthesis 20 provides relative pivotal and rotational movement between the adjacent vertebral bodies to maintain or restore motion substantially similar to the normal bio-mechanical motion provided by a natural intervertebral disc. More specifically, the endplate components 22, 24 are permitted to pivot relative to one another by way of the articulating central body 26 about a number of axes, including lateral or side-to-side pivotal movement about the longitudinal axis L and anterior-posterior pivotal movement about the transverse axis T. It should be understood that in one embodiment of the disclosure, the endplate components 22, 24 are permitted to pivot relative to one another about any axis that lies in the plane that intersects the longitudinal axis L and the transverse axis T. Furthermore, the endplate components 22, 24 are permitted to rotate relative to one another about a rotational axis R. Although the intervertebral disc prosthesis 20 has been illustrated and described as providing a specific combination of articulating motion, it should be understood that other combinations of articulating movement are also possible, such as, for example, relative translational or linear motion, and such movement is contemplated as falling within the scope of the present disclosure.

In some embodiments, the intervertebral disc prosthesis 20 may further provide a shock-absorbing function under compressive loads that are parallel to the rotational axis R. The shock-absorbing function may be provided by a mechanical spring configuration such as the ones shown in FIGS. 5-7 However, the mechanical spring configurations, as described below, are only meant to be examples and other mechanical spring configurations with different shapes and sizes have been contemplated.

Figure 5:
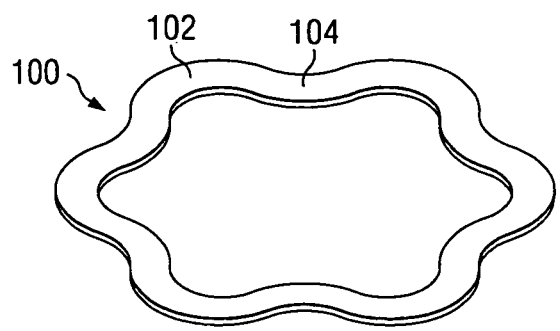
FIG. 5 is a perspective view of a wave spring washer.

More specifically, with respect to one embodiment, the mechanical compression component 50 may comprise a wave spring washer 100, as shown in FIG. 5. In this embodiment, the wave spring washer 100 is continuous and maintains a circumferentially complete 360 degrees. However, the wave spring washer 100 may not be continuous and may be provided with a slot (not shown). The wave spring washer 100 may be undulating and may include any number of peak sections 102 and valley sections 104. In addition, the wave spring washer 100 may be formed from a variety of elastic materials and may depend on the compressive load requirements of the intervertebral disc prosthesis. As a compressive load is applied to the endplate components 22, 24 of the intervertebral disc prosthesis 20, the end cap components 36, 38 are compressed against the wave spring washer 100 housed within the recess compartment 44 (not shown). The interior surface 56 of the upper end cap component 36 exerts a downward force onto the peak sections 102 of the wave spring washer 100 and the interior surface 58 of the lower end cap component 38 exerts an upward force onto the valley sections 104 of the wave spring washer 100. This action causes a deflection in the overall height (for the purposes of this description, the overall height is defined as the distance between the planes defined by the highest peak section 102 and the lowest valley section 104 of the wave spring washer 100) and a slight radial expansion of the wave spring washer 100, which in turn, produces a restoring force that will cause the wave spring washer 100 to spring back into its undeflected shape upon unloading of the compressive forces on the endplate components 22, 24.

Figure 6:
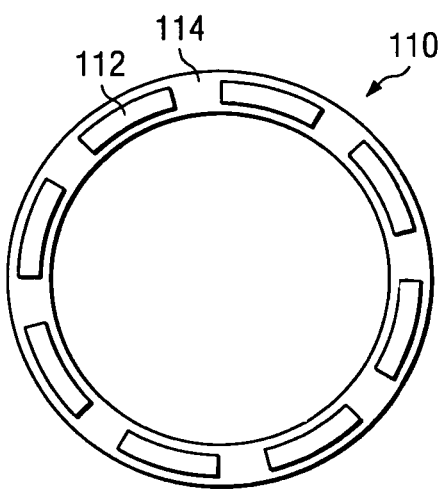
FIG. 6 is a perspective view of a ring-shaped leaf spring washer.

In another embodiment, the mechanical compression component 50 may alternatively comprise a ring-shaped leaf spring washer 110, as shown in FIG. 6. The ring-shaped leaf spring washer 110 may include any number of raised projections 112 extending from a circular ring base 114. In addition, the ring-shaped leaf spring washer 110 may be formed from a variety of elastic materials and may depend on the compressive load requirements of the intervertebral disc prosthesis. In operation, this embodiment has a similar type of shock-absorbing function as the one described above. As a compressive load is applied to the endplate components 22, 24 of the intervertebral disc prosthesis 20, the end cap components 36, 38 are compressed against the ring-shaped leaf spring washer 110 housed within the recess compartment 44 (not shown). The interior surface 56 of the upper end cap component 36 exerts a downward force onto the raised projections 112 of the ring-shaped leaf spring washer 110 and the interior surface 58 of the lower end cap component 38 exerts an upward force on the outer surface of the circular ring base 114 of the ring-shaped leaf spring washer 110. This action causes a deflection in the overall height of the ring-shaped leaf spring washer 110, which in turn, produces a restoring force that will cause the ring-shaped leaf spring washer 110 to spring back into its undeflected shape upon unloading of the compressive forces on the endplate components 22, 24.

Figure 7:
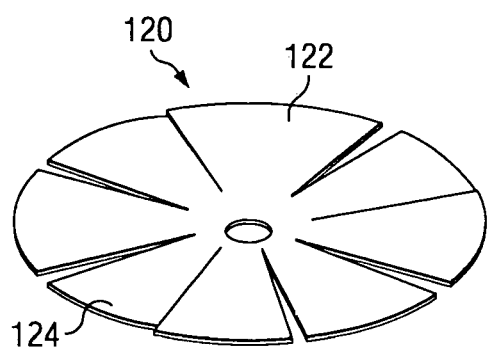
FIG. 7 is a perspective view of a leaf spring washer.

In another embodiment, the mechanical compression component 50 may alternatively comprise a leaf spring washer 120, as shown in FIG. 7. The leaf spring washer 120 may include any number of portions bent upwards 122 and portions bent downwards 124. In addition, the leaf spring washer 120 may be formed from a variety of elastic materials and may depend on the compressive load requirements of the intervertebral disc prosthesis. In operation, this embodiment has a similar type of shock-absorbing function as the one described above. As a compressive load is applied to the endplate components 22, 24 of the intervertebral disc prosthesis 20, the end cap components 36, 38 are compressed against the leaf spring washer 120 housed within the recess compartment 44 (not shown). The interior surface 56 of the upper end cap component 36 exerts a downward force onto the portions bent upwards 122 of the leaf spring washer 120 and the interior surface 58 of the lower end cap component 38 exerts an upward force on the portions bent downwards 124 of the leaf spring washer 120. This action causes a deflection in the overall height of the leaf spring washer 120, which in turn, produces a restoring force that will cause the leaf spring washer 120 to spring back into its undeflected shape upon unloading of the compressive forces on the endplate components 22, 24. In addition, the restoring force may be proportional to the elastic properties of the material used. Therefore, the restoring force may be varied by using different materials, as well as, employing different thicknesses for the mechanical compression component 50 of the articulating central body 26.

Figure 8:
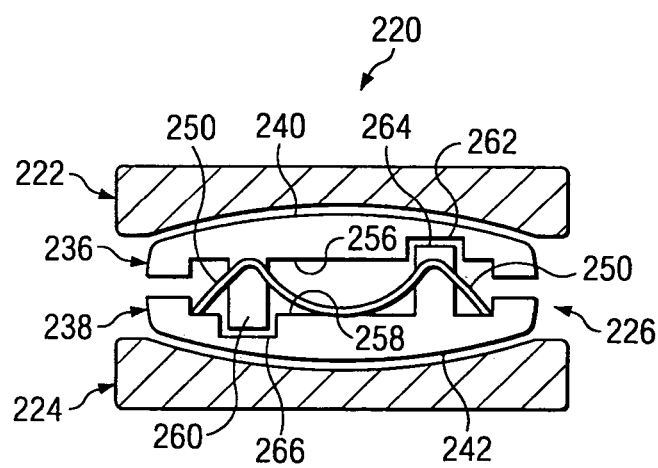
FIG. 8 is a cross sectional side view of an assembled intervertebral disc prosthesis according to an alternative embodiment of the present disclosure.

Now referring to FIG. 8, in an another embodiment of the present disclosure, an intervertebral prosthetic disc 220 may be used as the endoprosthesis 18 of FIG. 2. The intervertebral prosthetic disc 220 includes endplate components 222, 224 and an articulating central body 226. The articulating central body 226 includes end cap components 236, 238 and a mechanical compression component 250. The end cap components 236, 238 further include alignment keys 260, 264 extending from the interior surfaces 256, 258, respectively and alignment grooves 262, 266 recessing within the interior surfaces 256, 258, respectively. The alignment keys 260, 264 may be designed to mate with the corresponding alignment groove 262, 266 so that proper positioning of the end cap components 236, 238, with respect to each other, may be maintained as the endplate components 222, 224 articulate with the articulating surfaces 240, 242 of the end cap components 236, 238, respectively. In addition, the alignment keys 260, 264 may be designed to mate with the corresponding alignment groove 262, 266 to limit the maximum amount of deflection or compression of the end cap components 236, 238.

Although the alignment keys 260, 264 and corresponding alignment grooves 262, 266 are illustrated as being rectangular in cross section, other geometries have been contemplated, such as, for example, triangular, cylindrical or other shapes with a plurality of sides.

Figure 9:
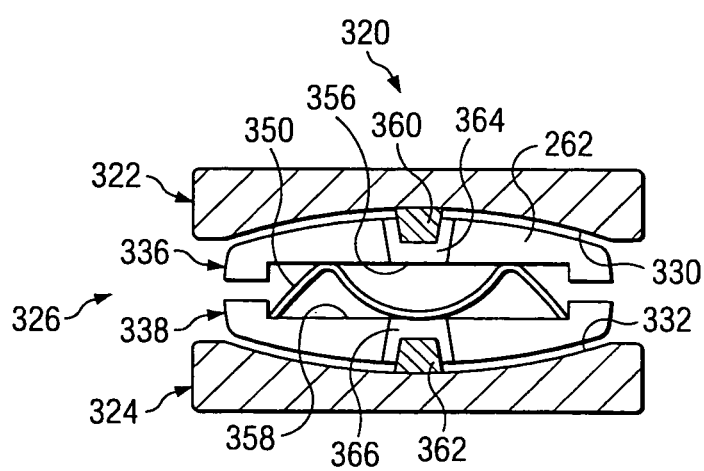
FIG. 9 is a cross sectional side view of an assembled intervertebral disc prosthesis according to an alternative embodiment of the present disclosure.

Now referring to FIG. 9, in still another embodiment of the present disclosure, an intervertebral prosthetic disc 320 may be used as the endoprosthesis 18 of FIG. 2. The intervertebral prosthetic disc 320 includes endplate components 322, 324 and an articulating central body 326. The endplate components 322, 324 include retaining elements 360, 362 disposed on the inner surfaces 330, 332, respectively. One example of a retaining element that may be used is a post with a reverse-taper geometry, as shown in FIG. 9. The articulating central body 326 includes end cap components 336, 338 and a mechanical compression component 350. The end cap components 336, 338 include central openings 364, 366 and are adapted to cooperate with the retaining elements 360, 362 of the endplate components 322, 324. In this embodiment, the retaining elements 360, 362 extend into the central openings 364, 366 of the end cap components 336, 338. It should be understood that the internal geometry of the central openings 364, 366 may be modified to provide the desired limit of motion for the articulation of the intervertebral disc prosthesis.

The present disclosure has been described relative to several preferred embodiments. Improvements or modifications that become apparent to persons of ordinary skill in the art after reading this disclosure are deemed within the spirit and scope of the application. For example, different shapes and sizes of the endoprosthetic device accordingly are contemplated.

Accordingly, it is understood that several modifications, changes, and substitutions are intended in the foregoing disclosure and, in some instances, some features of the disclosure will be employed without a corresponding use of other features. For example, the alignment key and corresponding alignment groove feature may be used in conjunction with the retaining element of the endplate components. It is also understood that all spatial references, such as "inner," "outer," "upper," "lower," are for illustrative purposes only and can be varied within the scope of the disclosure. Accordingly, it is appropriate that the appended claims be construed broadly and in a manner consistent with the scope of the disclosure.

What is claimed is:

1. A prosthetic device for insertion into an intervertebral space comprising:
    a first endplate component for engaging a first vertebral body, the first endplate component having a first articulating surface comprising a first retaining element protruding therefrom;
    a second endplate component for engaging a second vertebral body, the second endplate component having a second articulating surface comprising a second retaining element protruding therefrom; and
    an articulating central body component extending between the first and second endplate components, the articulating central body component comprising
        a first end cap component configured to articulate with the first endplate component, the first end cap component comprising a first central opening, the first retaining element extending through the first central opening,
        a second end cap component configured to articulate with the second endplate component, the second end cap component comprising a second central opening, the second retaining element extending through the second central opening, and
        a mechanical compression component having a series of circularly arranged portions integrally formed with one another, each portion extending at an angle between the first and second end cap components, each portion being positioned to contact a first location on the first end cap component and a second location on the second end cap component, the first and second locations being laterally offset from each other.

2. The prosthetic device of claim 1 wherein the mechanical compression component comprises a wave spring washer having a substantially continuous outer perimeter, and wherein the washer includes an undulating pattern having upper and lower contact points.

3. The prosthetic device of claim 1 wherein the mechanical compression component comprises a leaf spring washer with outwardly extending radial slits dividing the washer into a plurality of petals, the petals being arranged into upper petals and lower petals.

4. The prosthetic device of claim 1 wherein the mechanical compression component comprises a leaf spring washer including a plurality of annularly aligned louvers.

5. The prosthetic device of claim 1 wherein the first and second end cap components each comprise a wear-resistant surface.

6. The prosthetic device of claim 5 wherein each of the wear-resistant surfaces is made of a material selected from the group consisting of metal alloy, ceramic and polymer.

7. The prosthetic device of claim 1 wherein the first end cap component comprises an alignment key member and the second end cap component comprises a corresponding alignment groove member.

8. The prosthetic device of claim 7 wherein the alignment key member extends from an inner surface of the first end cap component to mate with the corresponding alignment groove member on an inner surface of the second end cap component.

9. The prosthetic device of claim 1 wherein the retaining element is a post having a reverse-taper geometry.

10. The prosthetic device of claim 1 wherein the first and second endplate components each include a bone contact surface for engaging the first and second vertebral bodies, respectively.

11. The prosthetic device of claim 10 wherein each of the bone contact surfaces are coated with a bone-growth promoting substance.

12. The prosthetic device of claim 1 wherein the first end cap component and the second end cap component include a recessed compartment for containing the mechanical compression component.

13. A prosthetic device for insertion into an intervertebral space comprising:
    a first endplate component comprising a first vertebral body contact surface and a first interior surface, the first interior surface comprising a first retaining element protruding therefrom;
    a second endplate component comprising a second vertebral body contact surface and a second interior surface, the second interior surface comprising a second retaining element protruding therefrom; and
    an articulating central body component interposed between the first interior surface and the second interior surface to permit motion between the first and second endplate components, wherein the articulating central body component comprises
        a first end cap component configured to articulate with the first endplate component, the first end cap component comprising a first central opening, the first retaining element extending through the first central opening,
        a second end cap component configured to articulate with the second endplate component, the second end cap component comprising a second central opening, the second retaining element extending through the second central opening, and a mechanical compression component, the mechanical compression component being arranged to permit compression of the first and second endplate components depending on the load force exerted on the first and second vertebral body contact surfaces, the compression component having a series of circularly arranged portions integrally formed with one another, each portion extending at an angle between the first and second end cap components, each portion being positioned to contact a first location on the first end cap component and a second location on the second end cap component, the first and second locations being laterally offset from each other.

14. The prosthetic device of claim 13 wherein the first and second end cap components each comprise a wear-resistant surface for articulating with the first and second interior surfaces, respectively.

15. The prosthetic device of claim 14 wherein each of the wear-resistant surfaces are smooth.

16. The prosthetic device of claim 13 wherein the first and second end cap components each comprise an alignment mechanism for aligning the first and second end cap components to ensure proper positioning with respect to each other.

17. The prosthetic device of claim 13 wherein the first and second interior surfaces each comprise a wear-resistant surface for articulating with the first and second end cap components, respectively.

18. The prosthetic device of claim 17 wherein each of the wear-resistant surfaces are smooth.

19. The prosthetic device of claim 13 wherein the first vertebral body contact surface is adapted to be affixed to a first vertebral body to prevent movement between the first endplate component and the first vertebral body.

20. A system for replacing an intervertebral disc, the system comprising:

a first endplate component for engaging a first vertebral body, the first endplate component having a first articulating surface comprising a first retaining element protruding therefrom;

a second endplate component for engaging a second vertebral body, the second endplate component having a second articulating surface comprising a second retaining element protruding therefrom; and an articulating central body component extending between the first and second endplate components, the articulating central body component comprising a mechanical compression component, wherein the articulating central body component provides motion between the first endplate component and the second endplate component, the articulating central body component comprising a first end cap component for articulating with the first endplate component, the first end cap component comprising a first central opening, the first retaining element extending through the first central opening and a second end cap component for articulating with the second endplate component, the second end cap component comprising a second central opening, the second retaining element extending through the second central opening, the first and second end cap components having a recessed compartment, wherein the mechanical compression component is disposed within the recessed compartment, the compression component contacting the first end cap component generally along a fixed radial first distance from a center of the articulating central body, and the compression component further contacting the second end cap component generally along a fixed radial second distance from the center, wherein the first and second distances are different.

21. The system of claim 20 wherein the mechanical compression component comprises a wave spring washer having a substantially continuous outer perimeter, and wherein the washer includes an undulating pattern having upper and lower contact points.

22. The system of claim 20 wherein the mechanical compression component comprises a leaf spring washer with outwardly extending radial slits dividing the washer into a plurality of petals, the petals being arranged into upper petals and lower petals.

23. A method for installing a prosthetic device between a first vertebral body and a second vertebral body, the method comprising:

providing a first endplate component for engaging a first vertebral body, the first endplate component having a first articulating surface comprising a first retaining element protruding therefrom;

providing a second endplate component for engaging a second vertebral body, the second endplate component having a second articulating surface comprising a second retaining element protruding therefrom;

providing an articulating central body component comprising a mechanical compression component; and inserting the articulating central body component between the first endplate component and the second endplate component, wherein the articulating central body component comprises a first and second end cap component, wherein the first end cap component articulates with the first endplate component, the first end cap component comprising a first central opening, the first retaining element extending through the first central opening and the second end cap component articulates with the second endplate component, the second end cap component comprising a second central opening, the second retaining element extending through the second central opening, the first and second end cap components including a recessed compartment, the mechanical compression component being disposed therein, and wherein the mechanical compression component contacts the first end cap component generally along a fixed radial first distance from a center of the articulating central body, and wherein the compression component further contacts the second end cap component generally along a fixed radial second distance from the center, the first and second distances being different.

* * * * *